United States Patent [19]

Evans et al.

[11] Patent Number: 5,250,033
[45] Date of Patent: Oct. 5, 1993

[54] PEEL-AWAY INTRODUCER SHEATH HAVING PROXIMAL FITTING

[75] Inventors: Michael A. Evans, Palo Alto; Raymond S. Figueroa, Jr.; Colin J. Nichols, both of Fremont, all of Calif.

[73] Assignee: Interventional Thermodynamics, Inc., Mountain View, Calif.

[21] Appl. No.: 967,602

[22] Filed: Oct. 28, 1992

[51] Int. Cl.$^5$ ............................................. A61M 5/178
[52] U.S. Cl. ........................... 604/160; 604/167; 604/161
[58] Field of Search ............. 604/160, 161, 264, 167, 604/164, 280

[56] References Cited

U.S. PATENT DOCUMENTS

| | | | |
|---|---|---|---|
| Re. 31,855 | 3/1985 | Osborne | 604/161 |
| 3,382,872 | 5/1968 | Rubin . | |
| 3,550,591 | 12/1970 | MacGregor | 128/214.1 |
| 3,653,388 | 4/1972 | Tenckhoff | 604/161 |
| 4,411,654 | 10/1983 | Boarini et al. | 604/165 |
| 4,412,832 | 11/1983 | Kling et al. | 604/164 |
| 4,430,081 | 2/1984 | Timmermans | 604/167 |
| 4,596,559 | 6/1986 | Fleischhacker | 604/170 |
| 4,772,266 | 9/1988 | Groshong | 604/160 |
| 4,983,168 | 1/1991 | Moorehead | 604/161 |
| 5,098,392 | 3/1992 | Fleischhacker et al. | 604/165 |
| 5,123,840 | 6/1992 | Nates | 604/313 |
| 5,141,497 | 8/1992 | Erskine | 604/160 |
| 5,167,634 | 12/1992 | Corrigan | 604/160 |

OTHER PUBLICATIONS

Angeion Corporation, Minneapolis, Minn., Antestat TM Hemostasis Valve Introducer brochure (2 pages).

Primary Examiner—John G. Weiss
Attorney, Agent, or Firm—Townsend and Townsend Khourie and Crew

[57] ABSTRACT

A peel-away introducer sheath includes a tube sheath having a splittable handle at its proximal end. A gas or liquid sealing valve or other fitting is secured to a proximal face of the handle and includes an axial passage typically having a diameter approximately equal to the lumen diameter of the sheath. The valve includes a threaded connector which is received in a counter bore formed in the handle. In this way, the sheath may be split apart leaving only the valve or other fitting in place on a catheter passing therethrough.

16 Claims, 2 Drawing Sheets

PEEL-AWAY INTRODUCER SHEATH HAVING PROXIMAL FITTING

BACKGROUND OF THE INVENTION

1. Field of the Invention

The present invention relates generally to medical devices and more particularly to introducer sheaths which are used for the transcutaneous introduction of catheters and other apparatus to a patient.

Introducer sheaths are commonly used in various medical procedures where a catheter is transcutaneously introduced to an interior body lumen or cavity, such as a blood vessel or a hollow body organ. Typically, the introducer sheath comprises a thin-walled sheath tube which is introduced through a previously formed needle penetration together with an internal stylet or obturator, where the stylet or obturator has a tapered distal end which extends from the sheath and dilates the previously formed hole as the sheath is advanced. After the combination of the sheath and stylet/obturator has been introduced, the stylet/obturator is removed, leaving a relatively large diameter working channel defined by the axial lumen of the sheath.

Various improvements in the design of such introducer sheaths have been proposed. Of particular interest to the present invention, peel-away introducer sheaths have been designed where the sheath is weakened along opposed axial lines to facilitate splitting when the proximal end of the sheath is pulled apart. Such peel-away sheaths are useful when it is desired to remove the sheath from around a catheter or other device which remains in place in the transcutaneous penetration. In particular, the sheath may be withdrawn and split or pulled apart to facilitate such removal. Without the ability to peel away the sheath, it would be impossible to remove the sheath over an enlarged proximal hub or housing on the catheter or other device which remains in place.

Another improvement comprises the attachment of a gas or liquid sealing valve on the proximal end of the sheath. The inclusion of the sealing valve permits the exchange of working catheters while the introducer sheath remains in place, with the valve minimizing gas or liquid loss during an interventional procedure.

The inventors herein have recognized a need to combine the benefits of a peel-away sheath with the placement of a sealing valve or other fitting at the proximal end of such sheath. In the case of sealing valves in particular, it has been recognized it would be desirable to permit catheter exchange through the sheath and, after placement of a final catheter, withdrawal and removal of the sheath while the final catheter remains in place. Additionally, in certain interventional and diagnostic procedures, it would be desirable to remove the valve to allow passage of a biopsy sample, stone, or other specimen too large to pass through the valve.

The mounting of valves and other fittings on the proximal end of a peel-away sheath, however, presents a number of difficulties. It will be very difficult to design valves and other complex fittings which are able to break away as the sheath is broken apart. Moreover, the attachment between the valve or other fitting and the sheath should not result in any reduction in the available diameter of the working channel, e.g. the valve and/or valve attachment should not provide a reduction of the inside diameter and constriction in the working channel. Additionally, the attachment of the valve or other fitting to the sheath should not compromise the structural integrity of the handle on the sheath in any way. That is, the presence of the fitting should not make it more difficult to break apart the handle or compromise the strength of the handle so that it becomes more fragile (i.e. it is more likely to be accidentally broken).

For these reasons, it would be desirable to provide peel-away introducer sheaths having fittings attached at their proximal ends, where the fittings and their manner of attachment do not reduce or constrict the working channel provided by the sheath. The attachment of the fittings should also not compromise the structural integrity of the sheath and/or associated sheath handle so that the sheath can be broken apart in a normal manner and will not be subject to failure. Additionally, it would be desirable to provide peel-away introducer sheaths which may be broken away, leaving in place a proximal fitting, so that the sheath may be withdrawn and removed without the requirement of breaking apart the fitting. Furthermore, it would be desirable to provide the physician with easy valve removal when it is necessary to pass a relatively large object, such as a biopsy sample or stone, through the sheath during a procedure.

2. Description of the Background Art

Peel-away introducer sheaths are described in U.S. Pat. Nos. 5,098,392; 4,983,168; 4,596,559; 4,412,832; and Re. 31,855. A splittable trocar which receives a tubular member in its proximal end is described in U.S. Pat. No. 3,653,388. Other splittable medical devices are described in U.S. Pat. Nos. 4,411,654; 3,550,591; and 3,382,872.

Non-splittable introducer sheaths having valves and other fittings permanently mounted on their proximal ends are available commercially from suppliers, such as Angeion Corp., Minneapolis, Minn. (e.g., the Angestat TM hemostasis valve introducer), and Arrow International, Inc. Reading, Pa.

SUMMARY OF THE INVENTION

According to the present invention, a peel-away introducer sheath incorporates a transition element at its proximal end. The transition element may be a hemostatic valve, gas or liquid sealing septum, multiport adapter, or any other fitting which can perform a useful function when attached to the proximal end of the sheath. The transition element is attached by a union to a splittable handle secured to the proximal end of the shaft, usually being detachably secured by a conventional detachable union, such as a threaded connection, bayonet connection, taper lock, or the like. In this way, the transition element may be removed and replaced, and more importantly may be released from the remainder of the sheath prior to splitting the sheath handle and pulling the sheath apart. In this way, the introducer sheath may be utilized in a conventional manner with the transition element in place, e.g. with a gas or liquid sealing valve to facilitate catheter exchange. The sheath may then be split apart after a final catheter has been introduced therethrough and the transition element disconnected, leaving only the transition element in place on the catheter.

In a first particular aspect of the present invention, the transition element includes an axial passage aligned with both the sheath lumen and handle aperture, where the diameter of the axial passage is at least as large as the diameters of the lumen and the aperture. In this way, the introducer sheath including the transition element is substantially free from constrictions which would reduce the effective diameter of the working channel.

In a second particular aspect of the present invention, the transition element includes a threaded male connector which is received in a threaded counter bore coaxially aligned with the aperture in the housing. A compressive seal is disposed about the male connector, and sealing is effected by axial compression which occurs when the transition element is mounted on the handle. This design minimizes the creation of radial forces within the aperture which might weaken or break the handle prior to the intentional breaking.

DESCRIPTION OF THE SPECIFIC EMBODIMENTS

Figure 1:
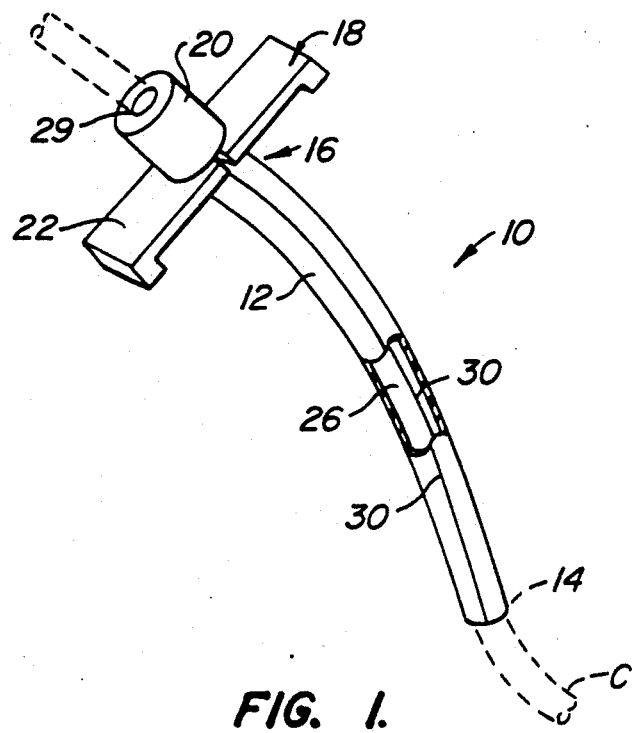
FIG. 1 illustrates a peel-away introducer sheath instructed in accordance with the principles of the present invention and having a catheter (shown in broken line) passing therethrough.

Referring now to the figures, a peel-away introducer sheath 10 constructed in accordance with the principles of the present invention comprises a thin-walled sheath tube 12 having a distal end 14, a proximal end 16, a handle 18 is attached to the proximal end, and a gas or liquid sealing valve 20 secured to a proximal face 22 of the handle 18, in a manner which will be described in greater detail hereinafter. The introducer sheath 10 defines an access lumen including a lumen 26 extending from the distal end 14 to the proximal end 16 of sheath tube 12, an aperture 28 (FIG. 3) formed in the handle 18, and an axial passage 29 formed in the gas or liquid sealing valve 20.

The introducer sheath 10 will be transcutaneously introduced to a desired body lumen or cavity, typically a blood vessel, hollow body organ, peritoneal space, or the like, by conventional techniques. Usually, the introducer sheath 10 will initially be placed over a stylet or obturator (not illustrated) which extends through the access lumen and includes a tapered distal end extending out of the distal end 14 of sheath tube 12. Using the tapered end of the stylet or obturator as a dilator, the introducer sheath can be passed into the target lumen through a previously formed hole, usually over a guidewire which has been introduced via needle puncture in a conventional manner. Once in place, the stylet or obturator will be removed, leaving the access lumen of the introducer sheath 10 available for use in subsequent procedures.

Figure 2:
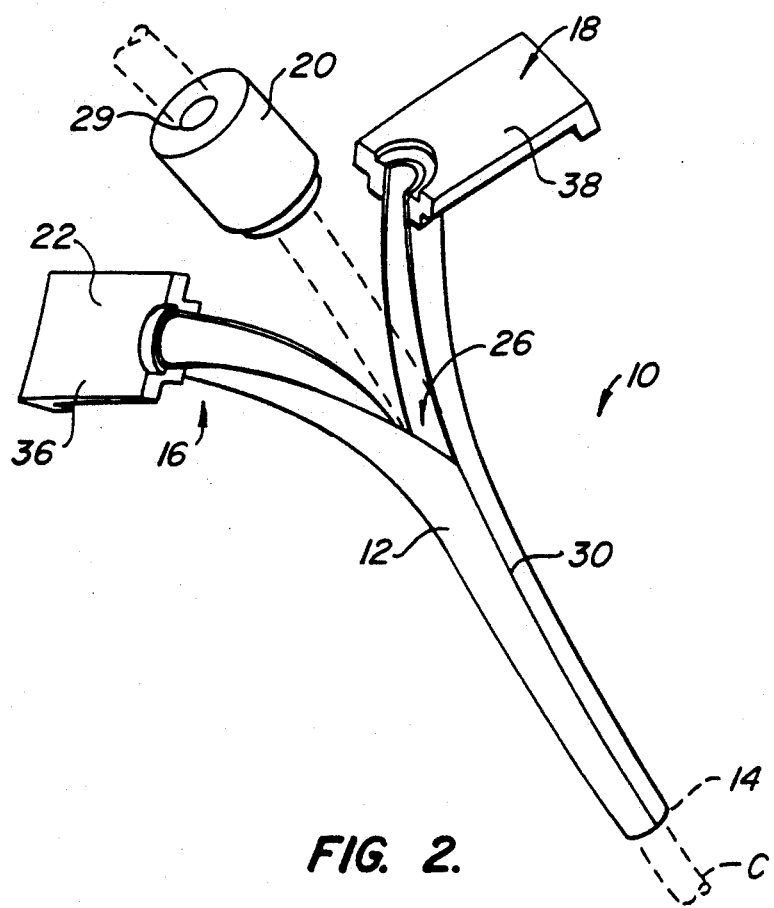
FIG. 2 illustrates the peel-away sheath of FIG. 1, shown with a proximal portion of the sheath pulled apart leaving a gas or liquid sealing valve in place on the catheter passing therethrough.

The sheath tube 12 is typically an elongated cylindrical tube formed from a thin-walled flexible plastic, such as polyethylene, tetrafluorethylene, fluorinated ethylene-propylene, or the like. The tube may be extruded by conventional means and will include a pair of thin or weakened axial grooves or lines 30, usually being diametrically opposed to each other. As described in more detail hereinafter, the thin lines 30 divide the tube into two elongate halves, where each half is attached to one half of the handle 18. In this way, the tubes may be pulled apart by breaking the handle 18 in half and pulling outwardly on the resulting handle "tabs," as best illustrated in FIG. 2. Alternatively, the material of the sheath tube may be axially oriented during the extrusion process, so that it will tear along an axial line without the need of a weakened axial path.

The dimensions of the tube sheath 12 are not critical. Typically, the tube sheath will have a length in the range from about 5 cm to 30 cm, usually in the range from about 5 cm to 15 cm. The internal diameter of the tube sheath 12 will typically be in the range from about 2 F (one F=0.33 mm) to 30 F, typically being in the range from about 5 F to about 16 F. Typically, the wall thickness of the tube sheath 12 will be in the range from about 0.03 mm to about 0.3 mm, usually being in the range from about 0.06 mm to about 0.15 mm.

The handle 18 includes a first tab 36 and a second tab 38, which tabs are formed after the handle is broken apart, as illustrated in FIG. 2. Handle 18 further includes a shank portion 40 (FIG. 3) extending from a distal face 42 of handle 18. The proximal end 16 of tube sheath 12 is fixedly received within the shank 40, with each half 26 of the tube being secured to one of the handled tabs 36 and 38, respectively. Even splitting or breaking apart of the handle 18 is facilitated by indentations or channels 46 which are formed in opposite sides of the handle and aligned with the weakened lines 30 present in the sheath tube 12.

As described thus far, the construction of the introducer sheath 10 is generally conventional. The construction of the handle 18, however, is modified according to the present invention in order to permit the attachment, usually the removable attachment, of a gas or liquid sealing valve 20, as will be described in detail hereinafter. The gas or liquid sealing valve 20 is illustrated as a hemostasis valve, but a wide variety of other transitional elements also may be secured to the proximal end of a peel-away introducer sheath according to the principles of the present invention. Other suitable transitional elements include sealing valves with side ports, single or multiple branched connectors for introduction or aspiration of gases or liquids, and the like.

Figure 3:
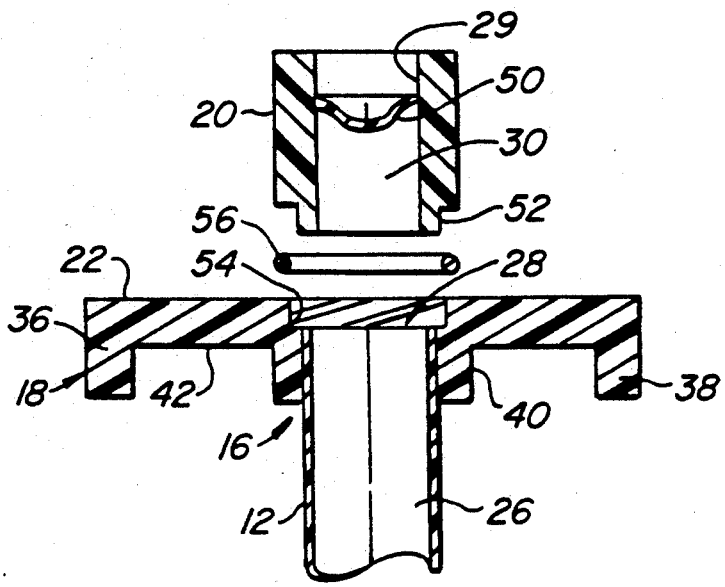
FIG. 3 is a detailed view of the proximal end of the peel-away sheath of FIG. 1, shown in cross-section.
Figure 4:
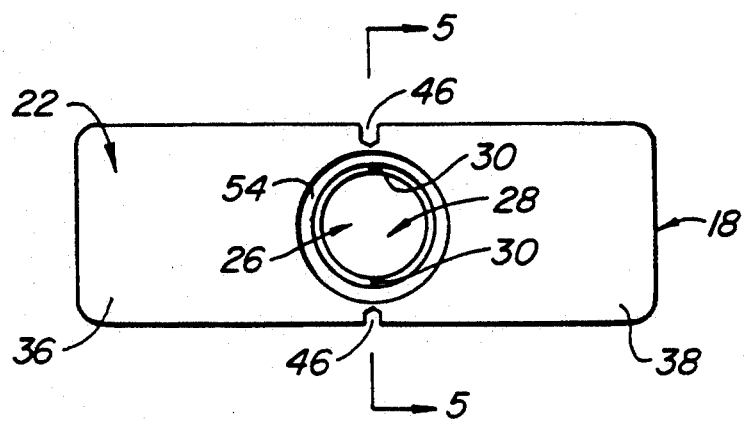
FIG. 4 is a top view of the peel-away sheath of FIG. 1, shown in the absence of the gas or liquid sealing valve.

Sealing valve 20 includes an internal valve member 50 (FIG. 3), typically in the form of a split septum 50. Conveniently, the split septum 50 will be generally hemispherical, with a concave surface disposed in the proximal direction. The concave surface will be able to receive a catheter C (as illustrated in broken line in FIGS. 1 and 2), while the convex surface will be able to seal against fluid pressure when in a closed configuration (as illustrated in FIG. 3) when the catheter C is removed.

Figure 5:
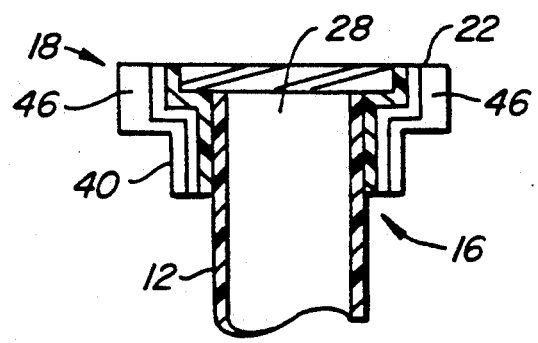
FIG. 5 is a cross-sectional view of a top portion of the sheath, taken along line 5—5 in FIG. 4.

The sealing valve 20 (or other transitional element) will be attached to the handle by a union, such as a threaded coupling which includes a threaded male connector 52 at its distal end. The threaded connector 52 is received within a threaded counter bore 54 which is coaxially aligned with the aperture 28 in handle 18. A compressive seal 56, such as an O-ring, is provided between the hemostasis valve 20 and the proximal surface 22 of the handle 18, so that a seal will be formed when the valve 20 is secured to the handle 18. Threaded connector 52 will preferably include a square male thread 53 received in a square female groove 55 formed in counter bore 54 (FIG. 5). The thread 53 and groove 55 will be arranged to permit mounting of the sealing valve 20 in one turn or less.

It will be appreciated that a wide variety of quick-disconnect connectors, such as bayonet mounts, friction locks, and the like, could also be utilized as a union for detachably securing the sealing valve 20 (or other transition elements) to the handle. Use of the illustrated threaded connection is preferred, however, as such a threaded connection provides minimal radially outward forces within the aperture 28. This is particularly true when a square thread configuration is employed for connection.

In use, the catheter C will be passed through the introducer sheath 10, as illustrated generally in FIG. 1. Introducer sheath 10 will maintain the desired access channel to the body lumen, permitting the catheter C to be removed and reintroduced or exchanged with one or more subsequent devices or catheters. After a final catheter has been introduced, the introducer sheath 10 can be withdrawn outwardly from the transcutaneous penetration, and the handle tabs 36 and 38 can be broken apart, as illustrated in FIG. 2. The sheath tube 12 can then be pulled apart along the thin lines 30, leaving the sealing valve 20 in place on the catheter C. In this way, the catheter sheath 10 and handle 18 may be removed from the catheter C, leaving only the sealing valve 20, which by itself presents only minimum interference with the remaining procedures. The sheath will have been positioned in a conventional manner, typically using a stylet which is then withdrawn, to a desired target lumen or body cavity.

Although the foregoing invention has been described in detail for purposes of clarity of understanding, it will be obvious that certain modifications may be practiced within the scope of the appended claims.

What is claimed is:

1. A peel-away sheath comprising:
   a sheath tube having a distal end, a proximal end, and a lumen therethrough, wherein said sheath is weakened along opposed axial lines to facilitate splitting into two halves;
   a splittable handle attached to the proximal end of the sheath tube and having a circular aperture aligned with the tube lumen, said handle being weakened at locations aligned with the weakened axial lines in the sheath tube so that the handle may be split and drawn apart to split the sheath tube along said axial lines; and
   a transition element removably attached to the splittable handle so that the element can be reattached after removal and having a circular axial passage aligned with the aperture in the handle and the lumen in the sheath, wherein the transition element is released from the handle when the handle is split apart.

2. A peel-away sheath as in claim 1, wherein the axial passage in the transition element has a diameter at least as large as that of the lumen in the sheath.

3. A peel-away sheath as in claim 1, wherein the transition element is selected from the group consisting of valves, and connectors.

4. A peel-away sheath as in claim 1, wherein the transition element includes a connector which is removably received in a counter bore in the splittable handle.

5. A peel-away sheath as in claim 4, wherein the connector and the counter bore have square mating threads.

6. A peel-away sheath comprising:
   a sheath tube having a distal end, a proximal end, and a lumen therethrough, wherein said sheath is weakened along opposed axial lines to facilitate splitting into two halves;
   a splittable handle attached to the proximal end of the sheath tube and having a circular aperture aligned with the tube lumen, said handle being weakened at locations aligned with the weakened axial lines in the sheath tube so that the handle may be split and drawn apart to split the sheath tube along said axial lines, wherein a threaded counter bore is formed in a proximal face of the handle co-axial with the aperture; and
   a transition element having a threaded male connector which is received in the counter bore and compression seal which is disposed about the connector, wherein the threads on the transition element and counter bore are square threads and whereby the transition element may be connected to or sealed against the handle without causing significant radial forces in the handle aperture.

7. A peel-away sheath as in claim 6, wherein the transition element is selected from the group consisting of valves, and connectors.

8. A peel-away sheath as in claim 6, wherein the handle is weakened by channels which are stepped to conform to the aperture and counter bore.

9. A peel-away sheath comprising:
   a sheath tube having a distal end, a proximal end, and a lumen therethrough, wherein said sheath is weakened along opposed axial lines to facilitate splitting into two halves; and
   a splittable handle attached to the proximal end of the sheath tube and having a circular aperture aligned with the tube lumen, said handle being weakened at locations aligned with the weakened axial lines in the sheath tube so that the handle may be split and drawn apart to split the sheath tube along said axial lines wherein a counter bore having square threads is formed in a proximal face of the handle co-axial with the aperture
   for detachably securing a transitional element, wherein said transitional element is released from the handle when the handle is split apart.

10. A peel-away sheath as in claim 9, wherein the square threads are arranged to receive the transition element in one turn or less.

11. An improved peel-away sheath of the type including a sheath tube and a splittable handle, wherein the handle may be split and drawn apart to tear the tube along opposed axial lines, wherein the improvement comprises a sealing valve attached to the handle by a union which permits mounting and demounting of the sealing valve without splitting of the handle and which releases the valve when the handle is split apart.

12. An improved peel-away sheath as in claim 11, wherein the union comprises a threaded connector on the sealing valve and a threaded counter bore in the handle.

13. An improved peel-away sheath as in claim 11, wherein the sealing valve defines an axial passage having a diameter at least as large as a lumen in the sheath tube.

14. A method for transcutaneously introducing a device through a sheath, said method comprising:
   positioning the sheath through tissue to a target lumen or body cavity;

introducing a device through the sheath to the target lumen or body cavity;

withdrawing the sheath over the device which remains in place;

removing a transition element from a proximal end of the sheath; and splitting the sheath after the transition element had been removed, whereby the transition element is left in place on the device.

15. A method as in claim 14, wherein the transition element is a sealing valve.

16. A method as in claim 14, wherein the transition element had been threadably secured to the proximal end of the sheath.

* * * * *